(12) United States Patent
Guo

(10) Patent No.: US 7,981,670 B2
(45) Date of Patent: Jul. 19, 2011

(54) METHOD OF ASSESSING DNA MUTABILITY

(75) Inventor: Yuyuan Guo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1024 days.

(21) Appl. No.: 11/400,539

(22) Filed: Apr. 6, 2006

(65) Prior Publication Data

US 2007/0238107 A1    Oct. 11, 2007

(51) Int. Cl.
  *C12N 15/00* (2006.01)
  *C12N 15/70* (2006.01)
  *C12N 15/74* (2006.01)

(52) U.S. Cl. .................. 435/320.1; 435/440; 435/476

(58) Field of Classification Search .................. None
  See application file for complete search history.

(56) References Cited

U.S. PATENT DOCUMENTS 5,300,431 A * 4/1994 Pierce et al. .................. 435/6
6,472,177 B1 * 10/2002 Szybalski et al. ............ 435/69.1

OTHER PUBLICATIONS

Kalnins et al., EMBO J. vol. 2, No. 4: 593-597, 1983.*
Steinmetz et al., Mol. Gen. Gent. vol. 200: 200-228, 1985.*
Ripley, L. S.; "Frameshift Mutation: Determinants of Specificity" (1990) Annu Rev Genet 24, 189-213.
Radman, M.; "DNA replication: One strand may be more equal" (1998) Proc Natl Acad Sci U S A 95, 9718-9.
Choi, T. J., Kim, S. C. & German, T. L.; "Toxicity of Tomato Spotted Wilt Virus Glycoprotein Signal Peptide . . . " (1999) Plant Pathol. J. 15, 313-318.
Ripley, L.S.; "Model for the participation of quasi-palindromic DNA sequences in frameshift mutation" (1982) Proc Natl Acad Sci USA 79, 4128-32.
Sinden R.R. and R.D. Wells; "DNA structure, mutations, and human genetic disease" (1992) Current Opinion in Biotechnology 3: 612-22.
Fink, S.P. et al.; "Mutagenicity in *Escherichia coli* of the major DNA adduct derived from the endogenous mutagen malondialdehyde" (1997) Proc Natl Acad Sci USA 94, 8652-7.
Smith, J., Modrich, P.; "Mutation detection with MutH, MutL, and MutS mismatch repair proteins" (1996) PNAS 93, 4374-4379.

* cited by examiner

*Primary Examiner* — Nancy Vogel
(74) *Attorney, Agent, or Firm* — Quarles & Brady LLP; Sara D. Vinarov

(57) ABSTRACT

The present invention relates to a method and a kit for assessing mutability of a DNA sequence of interest. The method involves using a mutation hotspot sequence as a standard to determine whether the DNA sequence of interest is more or less mutable than the hotspot sequence. The mutation events are detected using a bacterial system in which the DNA sequence of interest and the mutation hotspot sequence are each linked in-frame to a reporter gene such as a killer gene or a color gene so that any nonsense or out-of-frame frame shift mutation in the DNA sequence of interest or the mutation hotspot sequence can be reflected by a loss of the function of the reporter gene product. The kit of present invention contains one or more of the various vectors that are useful for practicing the method disclosed herein.

12 Claims, 8 Drawing Sheets

A: delete mutation at Hpa II site

SEQ ID NO: 12

B: correct sequence

TCGATGGCACCTCCGGCAAAGAGAGCC    SEQ ID NO: 13

*
5'-GGTACGATGGCACCTCCGGCAAA-3'    SEQ ID NO: 14

FIG. 2

5'-GGTACGATGGCACCTCAGGCAAAG-3'    SEQ ID NO: 15

↓ After the pgR106VP-VP1 was amplified.

5'-GGTACGATGGCACCTC GGCAAAG-3'    SEQ ID NO: 16

FIG. 6

A: Potential loop structure near hot spot (as template DNA)

```
3'-A G C T A C C G T    G T T T C T-5'          SEQ ID NO: 17
              G  C
              G  C
            A    G
              G
```

B: Mutated hot spot (in sense primer)

5' A C G A T G G C A T A T C C G G C A A A G A-3'    SEQ ID NO: 18

FIG. 7

METHOD OF ASSESSING DNA MUTABILITY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

DNA mutation is an important phenomenon that affects people in many different ways. For example, it has been associated with many diseases including various types of cancers. DNA mutation has also been found to be the primary strategy used by disease-causing microorganisms such as bacteria and viruses to evade or overcome treatments. Assessing the mutability of a DNA sequence has many important applications. For example, assessing the mutation rates of an oncogene or a suppressor gene in the presence and absence of an environmental factor will help determine whether the environmental factor increases the risk of cancer. In this regard, new methods for assessing DNA mutability will provide additional tools for studying DNA mutation and are therefore desirable in the art.

BRIEF SUMMARY OF THE INVENTION

The present invention relates to a method and a kit for assessing mutability of a DNA sequence of interest. The method involves using a mutation hotspot sequence as a standard to determine whether the DNA sequence of interest is more or less mutable than the hotspot sequence. The mutation events are detected using a bacterial system in which the DNA sequence of interest and the mutation hotspot sequence are each linked in-frame to a reporter gene such as a killer gene or a color gene so that any nonsense or out-of-frame frame shift mutation in the DNA sequence of interest or the mutation hotspot sequence can be reflected by a loss of the function of the reporter gene product. The kit of present invention contains one or more of the various vectors that are useful for practicing the method disclosed herein.

BRIEF DESCRIPTION OF THE SEVERAL VIEWS OF THE DRAWINGS

FIG. 2 shows the VP1 sequence around the translation initiation codon (ATG) in the parent plasmid. The Hpa II CCGG sequence in the parent plasmid was not mutated. The "*" indicates the deleted nucleotide "C" in the pgR106 vectored VP1. The fragment near this deletion hotspot was sequenced from 200 bp downstream of the VP1 fragment. The start codon was underlined.

FIG. 6 shows the point mutation in the Hpa II site. When the hotspot 5'-CCTCCGG-3' was mutated into 5'-CCT-CAGG-3', "A" was deleted after VP1 was sub-cloned into the pgR106 vector. This suggests that the second C in the Hpa II "CCGG" was deleted in this site-specific frameshift deletion mutation.

FIG. 7 shows that the loop structure is necessary for the hotspot mutation near the start codon in the VP1 fragment. A: Template DNA of the loop structure shows the hair-pin structure in the VP1 fragment (in template DNA 3'-5'). B: A newly synthesized strand showing the mutation that destroys the loop structure. The underlined letters were the bases that replaced "CC" in the hotspot.

DETAILED DESCRIPTION OF THE INVENTION

Figure 1:
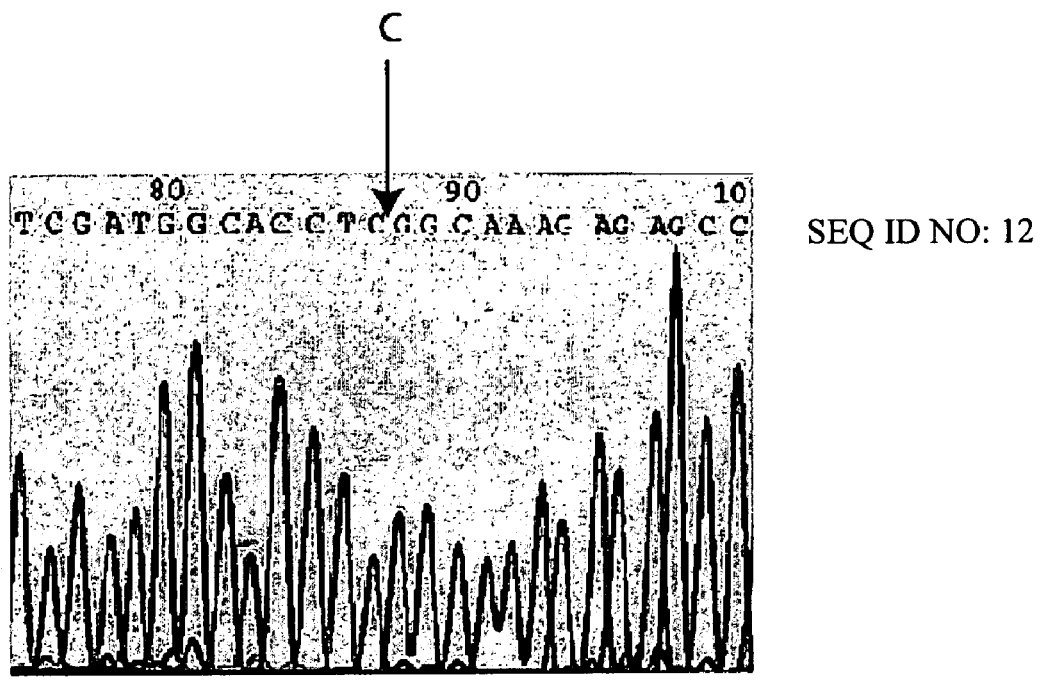
FIG. 1 shows the sequence of the pgR106 vectored VP1 around the translation initiation codon (ATG). A: A frame-shift deletion mutation occurred at the Hpa II site. The arrowhead points to the position of the deleted "C". B: The original VP1 sequence has the intact Hpa II site (CCGG).

The present invention provides a novel method for assessing mutability of a DNA sequence of interest by comparing the mutation rate of the DNA sequence of interest to that of a mutation hotspot sequence. In this method, the DNA sequence of interest and the mutation hotspot sequence are linked in-frame to a reporter gene that, upon expression in a bacterial cell, produces a polypeptide product whose function can be measured. Preferably, the reporter gene is a killer gene that, upon expression in a bacterial cell, produces a product that kills the cell, or a color gene that, upon expression in a bacterial cell, produces a product that can change the color of a bacterial colony. When a DNA construct containing a killer gene is expressed in a bacterial cell, the bacterial cell will survive only when there is mutation in the DNA construct that destroys the function of the killer gene. For example, an out-of-frame frame shift mutation in the mutation hotspot sequence or in the DNA sequence of interest will destroy the function of the killer gene. Therefore, whether the DNA sequence of interest is easier to mutate than the mutation hotspot sequence can be assessed by determining whether it can generate more bacterial colonies than the mutation hotspot sequence. When a DNA construct containing a color gene is expressed in a bacterial cell, whether the DNA sequence of interest is easier to mutate than the mutation hotspot sequence can be assessed by determining whether it can generate more bacterial colonies of a particular color than the mutation hotspot sequence.

The term "DNA sequence of interest" is used in the specification and claims to refer to a DNA sequence the mutability of which relative to a mutation hotspot sequence is determined by the method of the present invention.

The term "killer gene" is used in the specification and claims to refer to a DNA sequence that encodes a polypeptide product that is lethal to a bacterial cell. The term "color gene" is used in the specification and claims to refer to a DNA sequence that encodes a polypeptide product that can change the color of a bacterial colony. The term "bacterial colony reporter gene" is used in the specification and claims to refer to either a killer gene or a color gene as defined herein.

The term "loss-of-function mutation" is used in the specification and claims to refer to a mutation in a mutation hotspot sequence or a DNA sequence of interest linked in-frame to a bacterial colony reporter gene that destroys the function of the reporter gene. Examples of such loss-of-function mutations include out-of-frame frame shift mutations (e.g., insertions and deletions) and nonsense mutations (e.g., a substitution, insertion, and deletion that generates a stop codon that truncates a protein).

The term "mutation hotspot sequence" is used in the specification and claims to refer to a DNA sequence that can form a hairpin structure with a stem of 2 to 6 base pairs and a loop of 3 to 6 nucleotides. Preferably, the stem has 2 to 4, 2 to 3, or 2 base pairs. Also preferably, the loop has 3 to 5, 3 to 4, or 3 nucleotides. Typically, such a DNA sequence is GC rich, by which we mean that over 50%, 60%, 70%, or 80% of the nucleotides are either G or C. In one embodiment, the mutation hotspot sequence is selected from $CCN_1N_2N_3GG$, $CGN_1N_2N_3CG$, $GCN_1N_2N_3GC$, or $GG\ N_1N_2N_3CC$ wherein $N_1$, $N_2$, and $N_3$ can be any nucleotide. In a preferred embodiment, the mutation hotspot sequence CCTCCGG. It is noted that in general the longer the stem of the hairpin structure is, the easier it is for the mutation hotspot sequence to mutate.

Three expression vectors that are useful for the present invention are provided here. The first vector is an expression vector that contains a promoter operably linked to a DNA construct having a translation initiation codon (e.g., ATG), a DNA sequence of interest downstream of the initiation codon, a mutation hotspot sequence downstream of the initiation codon, and a bacterial colony reproter gene downstream of the initiation codon, wherein the translation initiation codon, the DNA sequence of interest, the mutation hotspot sequence, and the reporter gene are arranged in a way so that if the DNA construct is not mutated, a protein that comprises the amino acid sequence encoded by the reporter gene and maintains the function of the protein product of the reporter gene can be produced from the initiation codon in a bacterial cell and a nonsense or out-of-frame frame shift mutation in the mutation hotspot sequence or the DNA sequence of interest destroys the function of the reporter gene.

The second vector is an expression vector that contains a promoter operably linked to a DNA construct having a translation initiation codon (e.g., ATG), a mutation hotspot sequence downstream of the initiation codon, and a bacterial colony reporter gene downstream of the initiation codon, wherein the translation initiation codon, the mutation hotspot sequence, and the reporter gene are arranged in a way so that if the DNA construct is not mutated, a protein that comprises the amino acid sequence encoded by the reporter gene and maintains the function of the protein product of the reporter gene can be produced from the initiation codon in a bacterial cell and a nonsense or out-of-frame frame shift mutation in the mutation hotspot sequence destroys the function of the reporter gene. The DNA construct in the second vector does not contain a DNA sequence of interest.

The third vector is an expression vector that contains a promoter operably linked to a DNA construct having a translation initiation codon (e.g., ATG), a DNA sequence of interest downstream of the initiation codon, and a bacterial colony reporter gene downstream of the initiation codon, wherein the translation initiation codon, the DNA sequence of interest, and the reporter gene are arranged in a way so that if the DNA construct is not mutated, a protein that comprises the amino acid sequence encoded by the reporter gene and maintains the function of the protein product of the reporter gene can be produced from the initiation codon in a bacterial cell and a nonsense or out-of-frame frame shift mutation in the DNA sequence of interest destroys the function of the reporter gene. The DNA construction in the third vector does not contain a mutation hotspot sequence.

For the DNA constructs described above, as long as the mutation hotspot sequence and the DNA sequence of interest are linked in-frame with the bacterial colony reporter gene so that a polypeptide that contains the amino acid sequence encoded by the reporter gene and maintains the function of the protein product of the reporter gene can be produced from the initiation codon in a bacterial cell and a nonsense or out-of-frame frame shift mutation in the mutation hotspot sequence or the DNA sequence of interest destroys the function of the reporter gene, it is not critical as to how otherwise the mutation hotspot sequence, the DNA sequence of interest, and the reporter gene are arranged downstream from the translation start codon. For example, the mutation hotspot sequence can be upstream or downstream of the DNA sequence of interest. The mutation hotspot sequence can even be part of or located within the reporter gene as in the case of the VP1 gene provided in the example below. In one embodiment, the DNA sequence of interest and/or the mutation hotspot sequence are located upstream of the reporter gene.

The vectors described above can also contain an origin of replication. Optionally, in addition to the bacterial colony reporter gene as the selection marker, the vectors can also contain another selection marker such as an antibiotic resistance gene for cloning purposes (e.g., to select for transformation events). Also optionally, the vectors can contain a multiple cloning site for introducing a DNA sequence of interest, a mutation hotspot sequence, or a bacterial colony reporter gene into the vectors.

In one embodiment, the promoters used in the vectors are inducible promoters.

Many bacteriophage genes can be used as killer genes for the purpose of the present invention as their product can kill host bacterial cells. For instance, bacteriophage MS2 contains a gene encoding a bacterial lysis protein (Coleman, J. et al. 1983 J. Bacteriol. 153:1098-1100). Phage T4D contains genes encoding proteins that degrade cytosine-containing DNA in bacterial host cells (Kutter, E. and Wilberg, J. 1968 J. Mol. Biol. 38:395-411). Other T4 phage encode gene products that interfere with transcription of cytosine-containing DNA (Drivdahl, R. and Kutter, E. 1990 J. Bacteriol. 172:

2716-2727). Yet other T4 gene products are responsible for the disruption of the bacterial nucleoid (Bouet, J. et al. 1994 Gene 141:9-16).

In addition, other types of killer genes may be utilized. These include naturally-occurring or synthetic genes. A non-limiting example of a naturally-occurring gene that is suitable for use in the present invention is the hok gene product described by Gerdes et al. (1986 EMBO J. 5:2023-2029). Another example of naturally-occurring genes include colicin genes such as the colicin E3 gene from certain strains of *Escherichia coli*, the product of which are bactericidal for other sensitive strains of *Escherichia coli* and other related species (Diaz E. et al. 1994 Mol. Microbiol. 13:855-861). Another example of naturally-occurring genes include viral genes such as the VP1 gene from canine parvovirus type-2 (sequence disclosed in Reed, A. P. et al. 1988 J. Virol. 62:266-276) and viral genes that include a phospholipase $A_2$ domain which is known to be bactericidal. Another example of a naturally-occurring gene is the sacB gene from *Bacillus subtilis* or *Bacillus amyloliquefaciens*, the product of which is lethal to other sensitive bacteria if sucrose is provided in the culture media (Kaniga et al. 1991 Gene 109:137-141). Examples of man-made nucleic acid molecules that may be used in the present invention include sequences encoding peptides with bactericidal activity and endotoxin neutralizing activity for Gram-negative bacteria as described in U.S. Pat. No. 5,830,860.

In constructing and maintaining an expression vector containing a killer gene, the expression of the killer gene should be inhibited or the host bacterial cell should be modified so that it will not be killed by the product of the killer gene. As an example of the former, an inducible promoter can be used. The expression vector can be constructed and maintained in the absence of any inducer of the promoter and the mutability of a DNA sequence of interest can be assessed in the presence of an inducer. As for the latter, if an inhibitor of the killer gene product is known, such as arachidonyl trifluoromethylketone for $PLA_2$ (Tomioka H. 2005 J. Immunol. 175:6741-6749), the vector can be constructed and maintained in the presence of the inhibitor. Alternatively, if an immunity gene exists for a killer gene, such as the bacterial immunity E3 gene for the colicin E3 gene, the immunity gene can be provided in a host bacterial cell so that the host cell will not be killed by the product of the killer gene (Diaz E. et al. 1994 Mol. Microbiol. 13:855-861).

An example of a color gene that can be used in the present invention is the beta-galactosidase gene. When beta-galactosidase is produced in bacteria, it converts X-Gal (5-bromo-4-chloro-3-indolyl-[beta]-D-galactopyranoside) into a colored product, thereby converting a white colony into a blue colony in the presence said substrate.

In one aspect, the present invention relates to a method for assessing mutability of a DNA sequence of interest by introducing the first and second expression vectors described above into bacteria to obtain bacterial colonies. Preferably, the promoters, the mutation hotspot sequences and the bacterial colony reporter genes in the first and the second vectors are the same. The mutability of the DNA sequence of interest relative to the mutation hotspot sequence can then be determined by counting the number of colonies formed by the first and second vectors. When a killer gene is used in the vectors, all colonies will be counted. When a color gene is used in the vectors, only colonies with the color indicating a lack of function of the color gene product will be counted. A finding that the number of colonies formed by the first vector is more than twice of that formed by the second vector indicates that the DNA sequence of interest is more mutable than the mutation hotspot sequence and vise versa. The probability that a colony formed by the first vector contains a mutation in both the mutation hotspot sequence and the DNA sequence of interest is small and can be ignored for the purpose of the present invention.

In another aspect, the present invention relates to a method for assessing mutability of a DNA sequence of interest by introducing the first and third vectors described above into bacteria to obtain bacterial colonies. Preferably, the promoters and the bacterial colony reporter gene in the first and the second vectors are the same. The mutability of the DNA sequence of interest relative to the mutation hotspot sequence can then be determined by counting the number of colonies formed by the first and third vectors. When a killer gene is used in the vectors, all colonies will be counted. When a color gene is used in the vectors, only colonies with the color indicating a lack of function of the color gene product will be counted. A finding that the number of colonies formed by the third vector is more than half of that formed by the first vector indicates that the DNA sequence of interest is more mutable than the mutation hotspot sequence and vise versa. The probability that a colony formed by the first vector contains a mutation in both the mutation hotspot sequence and the DNA sequence of interest is small and can be ignored for the purpose of the present invention.

In another aspect, the present invention relates to a method for assessing mutability of a DNA sequence of interest by introducing the first vector described above into bacteria to obtain bacterial colonies. The mutability of the DNA sequence of interest relative to the mutation hotspot sequence can then be determined by analyzing whether the mutation hotspot sequence contains a loss-of-function mutation in a plurality of colonies. A skilled artisan is familiar with the techniques for this analysis. For example, either direct sequencing or PCR with a primer that contains the mutation hotspot sequence or its complement can be used for this purpose. As another example, if the mutation hotspot sequence contains a restriction site and the loss-of-function mutation (e.g., a deletion) destroys the restriction site, restriction enzyme digestion and the sizes of the fragments resulted from the digestion ca be analyzed for determining whether the mutation hotspot sequence contains a loss-of-function mutation. When a killer gene is used in the vector, any colony can be analyzed. When a color gene is used in the vector, only colonies with the color indicating a lack of function of the color gene product are analyzed. A finding that fewer than half of the colonies analyzed carry a loss-of-function mutation indicates that the DNA sequence of interest is more mutable than the mutation hotspot sequence and vise versa. The more colonies that one analyzes, the more accurate the result will be. The probability that a colony contains a mutation in both the mutation hotspot sequence and the DNA sequence of interest is small and can be ignored for the purpose of the present invention.

In another aspect, the present invention relates to a method for assessing mutability of a DNA sequence of interest by introducing the second and third expression vectors described above into bacteria to obtain bacterial colonies. Preferably, the promoters and the bacterial colony reporter genes in the second and third vectors are the same. The mutability of the DNA sequence of interest relative to the mutation hotspot sequence can then be determined by counting the number of colonies formed by the second and third vectors. When a killer gene is used in the vectors, all colonies will be counted. When a color gene is used in the vectors, only colonies with the color indicating a lack of function of the color gene product will be counted. A finding that the number of colonies formed by the third vector is more than that formed by the second vector indicates that the DNA sequence of interest is more mutable than the mutation hotspot sequence and vise versa.

After assessing the mutability of a DNA sequence of interest, one can identify the nature of the loss-of-function mutation in the DNA sequence of interest by any method familiar to a skilled artisan such as DNA sequencing of the mutated sequence.

In one embodiment, the present invention is used to assess the effect of a compound or other environmental factors on the mutability of a DNA sequence of interest. One can measure the mutation rate of the DNA sequence in the presence and absence of the compound or an environmental factor and determine whether mutation rate is higher in the presence of the compound or environmental factor.

In another embodiment, the present invention is used to analyze human genomic sequences to identify mutational hotspots either in general or under certain treatment conditions.

An advantage of the present invention is that the mutability of a DNA molecule can be determined without knowing its nucleotide sequence.

Under the present invention, a kit for assessing the mutability of a DNA sequence of interest can be provided. The kit can contain one or more of the following expression vectors and an instruction manual on using one or more of said vectors for assessing mutability of a DNA sequence of interest according to the methods of the present invention.

The first vector contains a promoter operably linked to a DNA construct having a translation initiation codon, a multiple cloning site downstream of the initiation codon, a mutation hotspot sequence downstream of the initiation codon, and a bacterial colony reporter gene downstream of the initiation codon, wherein when a DNA sequence of interest is introduced into the DNA construct at the multiple cloning site and if the DNA construct is not mutated, a protein that comprises the amino acid sequence encoded by the reporter gene and maintains the function of the protein product of the reporter gene can be produced from the initiation codon in a bacterial cell and a nonsense or out-of-frame frame shift mutation in the mutation hotspot sequence or the DNA sequence of interest destroys the function of the reporter gene.

The second vector contains a promoter operably linked to a DNA construct having a translation initiation codon, a mutation hotspot sequence downstream of the initiation codon, and a bacterial colony reporter gene downstream of the initiation codon, wherein the translation initiation codon, the mutation hotspot sequence, and the reporter gene are arranged in a way so that if the DNA construct is not mutated, a protein that comprises the amino acid sequence encoded by the reporter gene and maintains the function of the protein product of the reporter gene can be produced from the initiation codon in a bacterial cell and a nonsense or out-of-frame frame shift mutation in the mutation hotspot sequence destroys the function of the reporter gene.

The third vector contains a promoter operably linked to a DNA construct having a translation initiation codon, a multiple cloning site downstream of the initiation codon, and a bacterial colony reporter gene downstream of the initiation codon, wherein when a DNA sequence of interest or a mutation hotspot sequence is introduced into the DNA construct at the multiple cloning site and if the DNA construct is not mutated, a protein that comprises the amino acid sequence encoded by the reporter gene and maintains the function of the protein product of the reporter gene can be produced from the initiation codon in a bacterial cell and a nonsense or out-of-frame frame shift mutation in the DNA sequence of interest or the mutation hotspot sequence destroys the function of the reporter gene.

The vectors provided in the kit may have other features as the vectors described in connection with the method of the present invention.

In one embodiment, the kit of the present invention contains at least the first vector and the instruction manual.

In another embodiment, the kit of the present invention contains at least the first and second vectors and the instruction manual.

In another embodiment, the kit of the present invention contains at least the first and third vectors and the instruction manual.

In another embodiment, the kit of the present invention contains at least the second and third vectors and the instruction manual.

The invention will be more fully understood upon consideration of the following non-limiting example.

EXAMPLE

Mutation Hotspot Sequence and the Detection thereof by Selective Toxic Pressure

Materials and Methods

Construction of plasmids pgR106VP1, pCR3.1-VP1, and pCR3.1-gp53: Primers specific for canine parvovirus type-2 (CPV-2, Reed A P et al. J. Virol. 62:266-276, 1988) VP1 were used to amplify the VP1 ORF of CPV-2 with a PCR kit from QIAGEN. The sense primer was 5'-CCa tcg atG GCA CCT CCG GCA AAG AG-3' (SEQ ID NO:1). The Cla I sequence (lower case letters) was incorporated in front of the start codon (underlined). The antisense primer was 5'-CTA GGT GCT Agt cga cAT GTA ATA-3' (SEQ ID NO:2). The cloning site Sal I sequence (lower case letters) was incorporated within the neighbor sequence on the parent plasmid pVP1,2 which was sub-cloned from pBI429 (neomycin resistance) provided by Dr. Colin R. Parish (James A. Baker Institute, Corneal University). The stop codon TAA on VP1 ORF is not shown in the antisense primer. The PCR product purified with QIAquick PCR purification kit (QIAGEN) was cleaved with Sal I and Cla I restriction enzymes. The cleaved VP1 PCR product was sub-cloned into the potato virus x expression vector pgR106 (Chapman S et al. Plant J 2:549-57, 1992) provided by Baulcombe, D. (Sainsbury Laboratory John Innes Centere, Colney Lane, Norwish, UK, NR4 7UH). X-Gal (Nalgene) was used in TA cloning for selection. PCR primers and sequence primers were obtained from Integrated DNA Technologies, INC. (Coraiville, Iowa). As sub-cloning VP1 into the pgR106 plasmid was not successful and a deletion mutation occurred within the forward primer sequence, new primers were used to amplify the VP1 ORF with PCR. First, the PCR fragment was linked with pCR3.1-Uni Vector, a TA vector (INVITROGEN). Because Cla I is a methylation semi-sensitive restriction enzyme, the pCR 3.1-VP1 plasmid was first transformed into a methylation negative *E. coli* strain. After being cultured overnight, the plasmid was harvested with a plasmid purification kit from QIAGEN. The VP1 ORF in pCR3.1-VP1 was sequenced to confirm that the sequence was not mutated. The plasmid was cleaved with Cla I and Sal I, then a 2.2 kb band was isolated with the gel purification kit and linked with the pgR106 vector. After linking, the plasmid was transformed into methylation negative *E. coli* strains. Then, the plasmid pgR106VP1 was sequenced.

Bacterial Strains: E. coli methylation negative strain INV 110 (Invitrogen) and methylation positive strain JM109 (Promega) were used for transformation. The inducible E. coli strain BL21 (Promega) was transformed with T7 containing pCR3.1-VP1 and pCR3.1-gp53/Amp (Invitrogen) plasmids for testing the inhibition of the VP1 to bacteria.

DNA Sequencing: One primer 5'-AGTCAAGACCAAG-3' (SEQ ID NO:3) was designed from upstream sequence in pVP1,2 (parent plasmid) to confirm that the VP1 sequence in the parent plasmid was correct. Another primer 5'-CGAC-GAAGCTTACGCTGC-3' (SEQ ID NO:4) 200 bp downstream of the start codon was used to sequence from the other direction. One primer 5'-CCATAAGGGCCATTG-3' (SEQ ID NO:5) in the pgR106 vector was designed to sequence the VP1 ORF. T7 primer (Invitrogen) was used to sequence the VP1 ORF in pCR3.1-VP1. The sequence work was done at the Biotech Center, University of Wisconsin-Madison.

DNA mapping: In order to test whether the mutation is vector specific, different VP1 containing plasmids were cleaved with Hpa II (Promega) for DNA mapping. Because VP1 contains two Hpa II sites and there are 478 base pairs between them, a DNA fragment of about 500 bp would be generated when non-mutated VP1 was cleaved by Hpa II. If the first CCGG was not mutated, a DNA band of about 500 bp would be generated regardless the VP1 containing vectors used. Different plasmids were cleaved with Hpa II and run on 2% agarose gel to for DNA mapping.

Site mutation to determine the hotspot sequence: We hypothesized that the Hpa II site was necessary for the hotspot. With point mutation, "CCGG" was mutated into "CAGG". The sense primer was designed as GCATCGATG-GCACCTCAGGCAAAGA (C in CCGG was substituted into A, SEQ ID NO:6). The amplified VP1 fragment was sub-cloned into the pgR106 vector and sequenced.

In order to test whether the loop structure is necessary for the hotspot, the original sequence GCATCGatgGCA CCTccggCAAAGA (SEQ ID NO:7; underlined base pairs indicate potential C-G pairs; lower case letters represent the start codon and the Hpa II site) was changed into ATGGCAat-TCCGGCAAAGA (SEQ ID NO:8) as the sense primer to amplify VP1 (lower case letters indicate the bases that were mutated from CC).

Toxicity assay: It was hypothesized that the VP1 was forced to mutate because the intact VP1 was toxic to E. coli. The non-mutated VP1 would kill the cells, thus there would be no colonies after E. coli propagation. The toxicity of the VP1 was tested by the growth inhibition of two transformed E. coli as described by Choi T J et al. The -Plant Pathology Journal 15:313-318, 1999. In order to test this, the VP1 ORF was sub-cloned into an inducible TA cloning vector, the pCR3.1-Uni containing the T7 promoter. One primer 5'-GCAGCGTAAGCT-3' (SEQ ID NO:9) within the VP1 was designed to sequence and confirm that the VP1 was ligated behind the T7 promoter in the correct orientation. Another unrelated ORF gp53 (Donis R O Vet Clin North Am Food Anim Pract 11:393-423, 1995) in S-gp53-pGEM plasmid provided by Donis R. O. (University of Nebraska) was amplified with PCR, the sense primer being 5'-CCATCGATG-GACTTGCATTGCAAACCTG-3' (SEQ ID NO:10) and the antisense primer being 5'-GTCGACTCACCCTGAGGCCT-TCTGTTC-3' (SEQ ID NO:11). The new plasmids pCR3.1-gp53 and pCR3.1-VP1 were transformed into a competence E. coli BL21 strain because it contains a T7 DNA polymerase gene which can be induced by Isopropyl β-D-thiogalactoside (IPTG) (GIBCOBRL). When the E. coli cells were cultured to 0.3 in $OD_{600}$ at 37° C., the IPTG was added to a final concentration of 14 mM. The E. coli cells were cultured in 50 μg Ampicillin/ml LB medium to prevent the lost of plasmids. The final culture volume was 15 ml. Every hour, 100 μl was taken from the tubes to test the value of $OD_{600}$. Both pCR3.1-VP1 and pCR3.1-gp53 plasmids transformed E. coli had three replications. The value of $OD_{600}$ was the average of the three replications.

Results

The construction of the potato virus x expression vector pgR106-VP1: The VP1 ORF was ligated with the pgR106 vector and transformed into a methylation negative E. coli strain for amplification. However, we hardly observed any colony forming unit (CFU) that contained the 2.2 kb VP1 ORF insertion. All VP1 ORF's in the pgR106-VP1 vector were found to be mutated at the Hpa II site. We had sequenced 18 constructed plasmids and found that 9 contained a deletion mutation ("C" deleted) (Table 1, pgR106-VP1). The hotspot site point mutation (C→A) in the VP1 can help E. coli survive (Table 1, point C-A mutation). However, when the loop structure in the hotspot was mutated, the VP1 lost the potential mutation site. Without mutation, there would be no bacterial colonies (Table 1, loop mutation).

TABLE 1

|  | pgR106-VP1 | point C-A mutation | loop mutation |
|---|---|---|---|
| Total # | 18 | 7 | 5 |
| Self-ligation # | 9 | 4 | 5 |
| mutation # | 9 | 2 | 0 |

The total # indicates the number of constructed plasmids which were sequenced. Self-ligation # indicates the number of plasmids that were found not to have the VP1 ORF insertion. Mutation # indicates the number of constructed plasmids that had the mutated VP1 fragment (either the site specific deletion or the point mutation).

Figure 2:
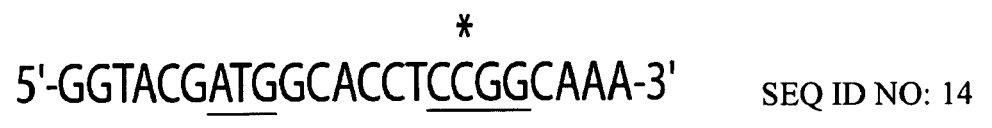

A sequence assay for the VP1 in different vectors: The VP1 fragment sequences from both the PCR and TA cloning resource used in constructing the pgR106-VP1 were the same. The sequence near Hpa II was found to be 5'-TCG ATG GCA CCT ↓CG GCA AAG AGAGCC-3' (SEQ ID NO: 12, ↓ indicates the delete position) (FIG. 1A). There was not an impacted peak that indicated that a nucleotide was covered. The correct sequence is 5'-TCG ATG GCA CCT CCG GCA AAG AGAGCC-3' (SEQ ID NO: 13, FIG. 1B). To confirm the result, the VP1 ORF in the pgR106-VP1 was sequenced from other direction to show that the "C" was missed. Initially, it was thought that the forward primer was not synthesized correctly because the mutation site was within the primer. Therefore, a newly synthesized primer was used to repeat the experiment and the same frameshift deletion mutation was observed. To test the possibility that the methylation negative E. coli strain could not repair the deletion mutation, the VP1 ORF was re-amplified with PCR and inserted into the pgR106 vector directly. The new pgR106-VP1 was transformed into a methylation positive E. coli strain, JM109. The frameshift deletion mutation was observed again. To test whether the mutation was from the parent plasmid, the VP1 in the parent plasmid pVP1,2 was sequenced and found to have the correct sequence shown in FIG. 2 (SEQ ID NO:14).

Figure 3:
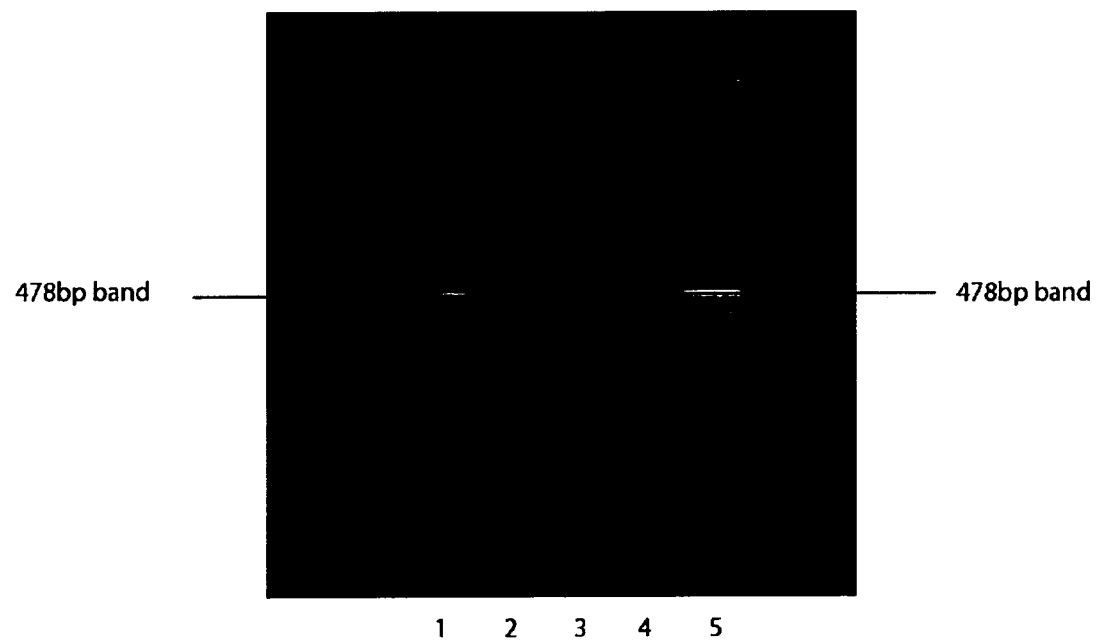
FIG. 3 shows the Hpa II mapping of the VP1 fragments in different vectors. There are two "CCGG" within the VP1 fragment with 478 bp between them. Thus, a band near 500 bp would occur whenever VP1 is subject to Hpa II DNA mapping. If the first "CCGG" of the pgR106-VP1 is mutated, the 478 bp band would not occur. Lane 1 and Lane 5: 100 bp ladder DNA marker. Lane 2: the pCR3.1-VP1 Hpa II DNA mapping. Lane 3: the pgR106-VP1 Hpa II DNA mapping. Lane 4: the pBI121-VP1 Hpa II DNA mapping. The pgR106-VP1 missed the 478 bp band when treated with Hpa II, while both pCR3.1-VP1 and pBI121-VP1 had this band as the lines indicate. The VP1 fragment mutated only when it was sub-cloned into the pgR106 vector. This was a vector specific mutation.
Figure 4:
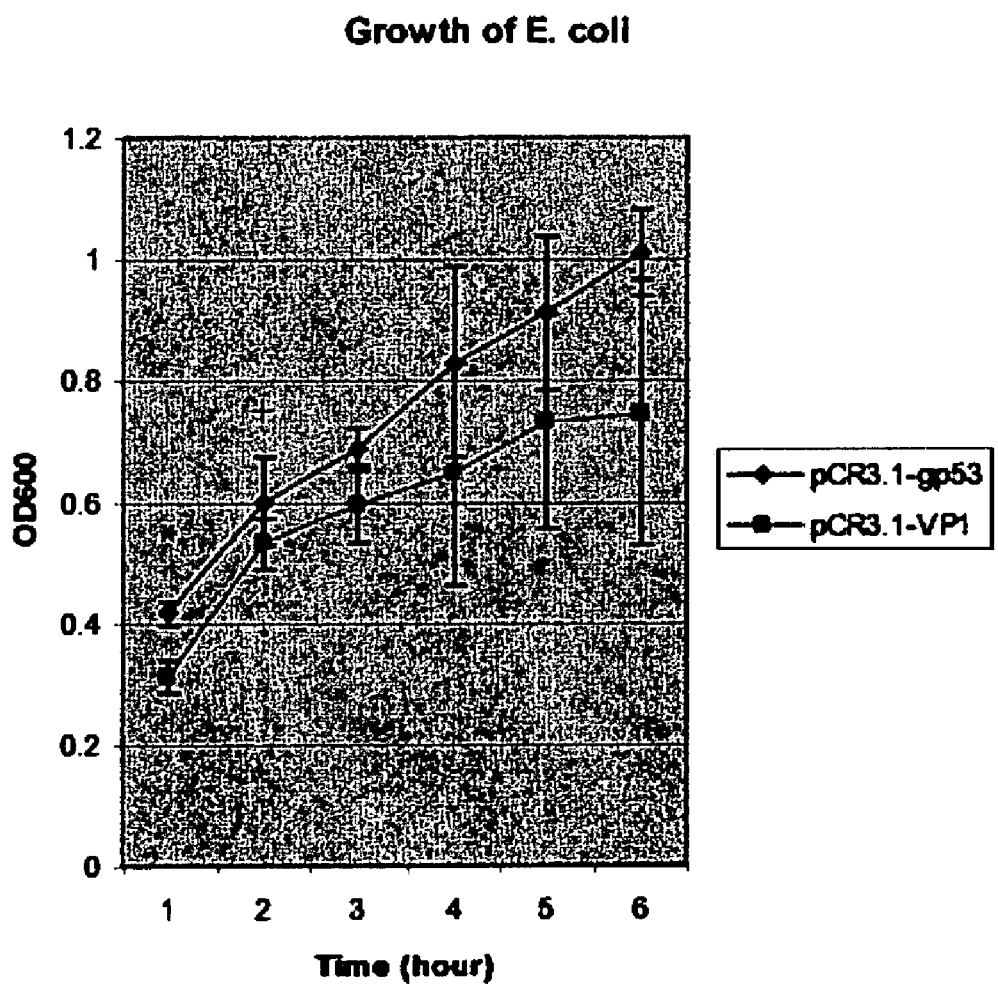
FIG. 4 shows the growth of E. coli after Isopropyl β-D-thiogalactoside (IPTG) was added to the medium. The control plasmid pCR3.1-gp53 transformed E. coli grew faster than the pCR3.1-VP1 transformed E. coli. At hour 0, the OD600 values of both plasmid transformed E. coli were 0.3 and the inducer IPTG was added. At hour 1 of culture, the OD600 values were significant different (P<0.01, T-test) as marked by *. At hour 2 of culture, the OD600 values were also different (P<0.1, T-test), which is marked as +. Statistics analysis was done with OD600 values in three replications. The growth of pCR3.1-VP1 transformed E. coli gradually increased.
Figure 5:
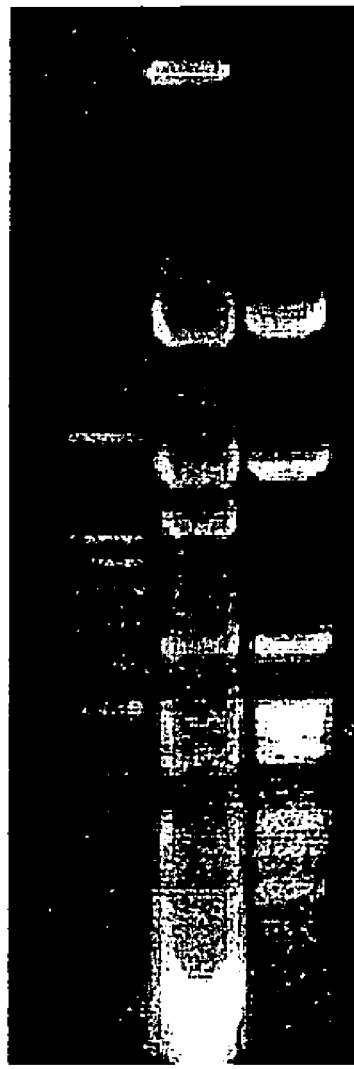
FIG. 5 shows Hpa II DNA mapping of the pCR3.1-VP1 plasmid. Hpa II mapping of pCR3.1-VP1 altered when an inducer IPTG was added. Lane 1: the 100 bp ladder marker. Lane 2: the pCR3.1-VP1 plasmid Hpa II DNA mapping. Lane 3: the Hpa II DNA mapping of the pCR3.1-VP1 after IPTG was added. The pattern of Hpa II DNA mapping changed, suggesting the Hpa II sequence was altered.
Figure 8:
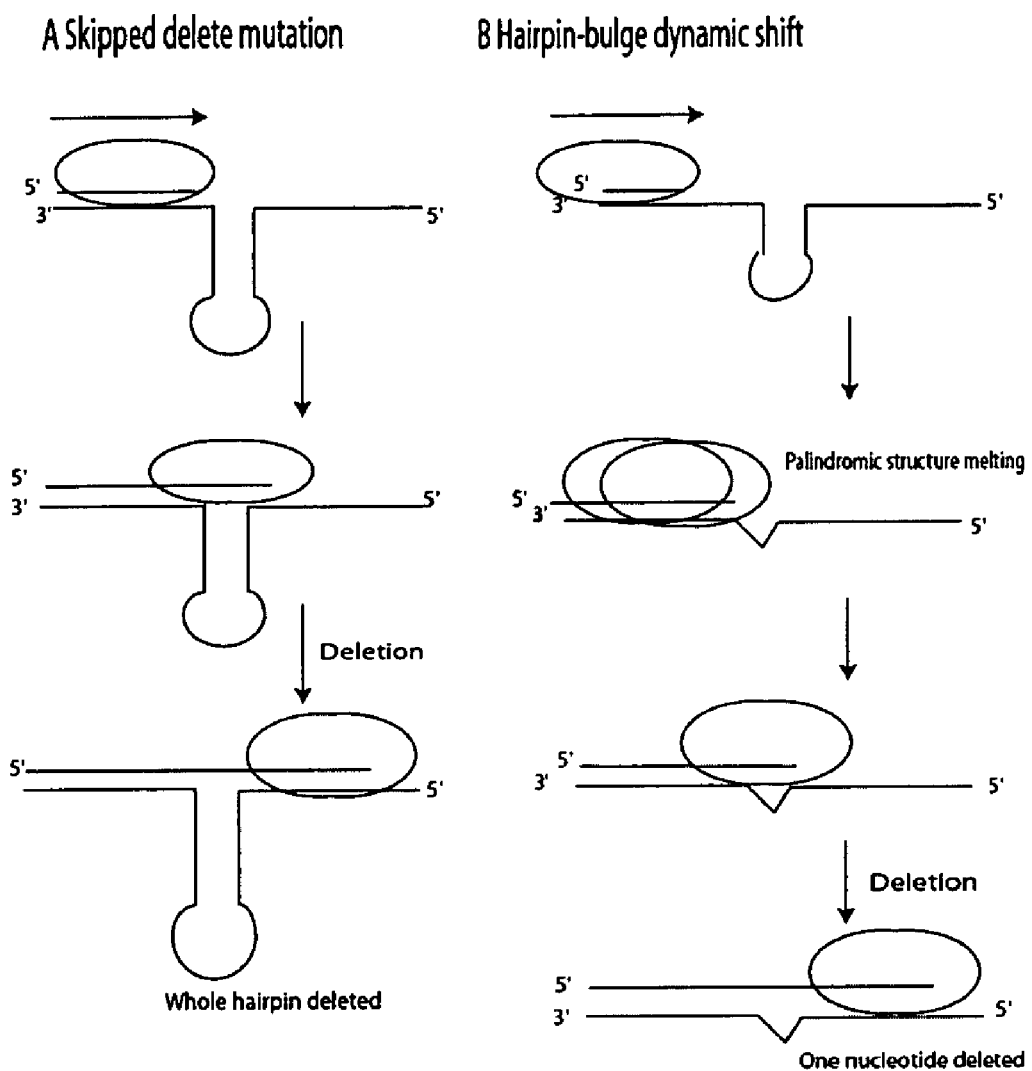
FIG. 8 compares the skipped deletion model and hairpin-bulge dynamic shift model. Skipped delete mutation is shown in (A). The loop structure was skipped and the whole loop was deleted. The dynamic shift model shows the hairpin-bulge was in a dynamic movement (B). Because of the short palindromic sequence, the hairpin structure was melted easily. When the bulge structure was formed, one nucleotide was skipped.

The site specific frameshift deletion mutation was vector specific: To test whether the deletion mutation was vector (pgR106) specific, the VP1 fragment in the parent vector and the pCR3.1-Uni vector was sequenced. The sequences were correct. The VP1 fragments in different vectors were compared by DNA mapping and the deletion happened only in the pgR106 vector (FIG. 3). After being treated with Hpa II, only the pgR106-VP1 did not have the 478 bp DNA band, while other VP1 containing vectors had the band. This confirmed that the CCGG (Hpa II restriction site) in the pgR106-VP1 had one "C" deleted. It was found that the pgR106 contains a cryptic promoter which was recognized by bacteria when the plasmid was amplified in the *E. coli* (data not shown). The VP1 was expressed under the cryptic promoter.

The toxicity of the VP1 and the mutation under the toxic pressure: Because the VP1 was expressed in *E. coli* when the plasmid was amplified, the unexpected expression interrupted the sub-cloning work. Only the mutated VP1 would make *E. coli* survive. We hypothesized that VP1 was toxic to *E. coli*. Under the induction of IPTG, the growth of the pCR3.1-VP1 transformed *E. coli* was inhibited compared with the pCR3.1-gp53 transformed *E. coli*. The cell numbers of both pCR3.1-VP1 and pCR3.1-gp53 transformed bacteria were measured in the presence of IPTG (FIG. 4). At the start point (0 hour), both transformed *E. coli* were 0.3 at $OD_{600}$. At one hour, the bacterial growth was significantly different. The growth of pCR3.1-VP1 transformed *E. coli* was highly inhibited compared with the control plasmid pCR3.1-gp53 transformed *E. coli*.

Gradually, after six hours of culture, the number of *E. coli* in pCR3.1-VP1 transformed *E. coli* increased. We tested if this was the caused by a mutation in the VP1 fragment. To do this, we evaluated the presence of the VP1 protein by Western blot in both pCR3.1-VP1 and pCR3.1-gp53 transformed cells. Neither expressed VP1 protein, indicating that pCR3.1-VP1 transformed *E. coli* did not express the VP1 protein. Trace of VP1 might be expressed at beginning when inducer was added. However, over time, the mutated pCR3.1-VP1 transformed *E. coli* replaced the non-mutated plasmid transformed *E. coli*. This was demonstrated by the Hpa II DNA mapping. After six hours of culture with inducer in the medium, both plasmids were isolated and cleaved with Hpa II for DNA mapping (FIG. 5). The Hpa II DNA mapping of pCR3.1-VP1 altered when an inducer IPTG was added, indicating that when the VP1 was expressed, under toxic pressure, the VP1 gene had undergone mutation. After six hours of culture, the toxicity of VP1 did not exist anymore. The increase in the $OD_{600}$ value was caused by VP1 mutation.

The hotspot site determined by Hpa II point mutation and loop substitute mutation: Because the deletion site was always linked with the Hpa II site, we tested whether the palindromic sequence of Hpa II was important for the mutation and which "C" was deleted by changing "CCTCCGG" to "CCTCAGG" (FIG. 6). We found that "A" was deleted as a result of the deletion mutation (FIG. 6) and therefore it was the second "C" of the Hpa II site that was deleted in the site-specific frameshift deletion mutation. While the deleted "A" accounted for two colonies obtained (Table 1, point C-A mutation), we observed another point mutation in the third non-self ligation colony: a frameshift mutation (+1 mutation) in a sequence 120 bp downstream of the site "CAGG" while the site "CAGG" itself did not mutate. This suggests that any mutation that destroys the toxic domain within VP1 could make the *E. coli* survive. It is also noted that when the Hpa II site was mutated (point C-A mutation), fewer colonies formed (Table 1).

There is a loop structure near the start codon (FIG. 7A). To test whether this loop structure is necessary for the site-specific frameshift mutation, the loop sequence was mutated (FIG. 7B) to destroy the loop structure. After the mutated VP1 fragment was cloned into the pgR106 vector, we failed to obtain any VP1-containing colonies (Table 1, loop mutation). This suggests that the loop structure is necessary for the site-specific frameshift deletion mutation.

Without intending to be limited by theory, we propose a new model in deletion mutation to explain the observed site-specific deletion mutation. Rather than the result of a skipped deletion (FIG. 8A) in which more than one nucleotides are expected to be deleted, we believe that the DNA polymerase approaches and skips one nucleotide instead of the whole loop structure. The template DNA strand is in a movement rather than being still. We call this model the hairpin-bulge dynamic shift model (FIG. 8B). During DNA synthesis, secondary structure is in a dynamic movement and the hair-pin structure changes into a bulge structure when a DNA polymerase approaches. The bulged nucleotide is skipped by the DNA polymerase in the hotspot site.

The present invention is not intended to be limited to the foregoing example, but encompasses all such modifications and variations as come within the scope of the appended claims.

I claim:

1. A kit comprising:

two expression vectors selected from the group consisting of
   (1) an expression vector comprising a promoter operably linked to a DNA construct that comprises a translation initiation codon, a multiple cloning site downstream of the initiation codon, a mutation hotspot sequence downstream of the initiation codon, and a bacterial colony reporter gene downstream of the mutation hotspot sequence, wherein when a DNA sequence of interest is introduced into the DNA construct at the multiple cloning site, a protein that comprises the amino acid sequence encoded by the reporter gene and maintains the function of the protein product of the reporter gene can be produced from the initiation codon in a bacterial cell and a loss-of-function mutation in the mutation hotspot sequence or the DNA sequence of interest destroys the function of the reporter gene,
   (2) an expression vector comprising a promoter operably linked to a DNA construct that comprises a translation initiation codon, a mutation hotspot sequence downstream of the initiation codon, and a bacterial colony reporter gene downstream of the mutation hotspot sequence, wherein the translation initiation codon, the mutation hotspot sequence, and the reporter gene are arranged in a way so that a protein that comprises the amino acid sequence encoded by the reporter gene and maintains the function of the protein product of the reporter gene can be produced from the initiation codon in a bacterial cell and a loss-of-function mutation in the mutation hotspot sequence destroys the function of the reporter gene, and (3) an expression vector comprising a promoter operably linked to a DNA construct that comprises a translation initiation codon, a multiple cloning site downstream of the initiation codon, and a bacterial colony reporter gene downstream of the initiation codon, wherein when a DNA sequence of interest or a mutation hotspot sequence is introduced into the DNA construct at the multiple cloning site a protein that comprises the amino acid sequence encoded by the reporter gene and maintains the function of the protein product of the reporter gene can be produced from the initiation codon in a bacterial cell and a loss-of-function mutation in the DNA sequence of interest or the mutation hotspot sequence destroys the function of the reporter gene, wherein the two expression vectors are (1) and (2), expression vectors (1) and (3), or expression vectors (2) and (3); and an instruction manual on using two of said vectors for assessing mutability of a DNA sequence of interest.

2. The kit of claim 1, wherein the reporter gene is a killer gene, the product of which can be lethal to a bacterial cell.

3. The kit of claim 1, wherein the reporter gene is a color gene, the product of which can change the color of a bacterial colony.

4. A kit comprising:
two expression vectors selected from the group consisting of
(1) an expression vector comprising a promoter operably linked to a DNA construct that comprises a translation initiation codon, a multiple cloning site downstream of the initiation codon, a mutation hotspot sequence downstream of the initiation codon, and a bacterial colony reporter gene downstream of the mutation hotspot sequence, wherein when a DNA sequence of interest is introduced into the DNA construct at the multiple cloning site, a protein that comprises the amino acid sequence encoded by the reporter gene and maintains the function of the protein product of the reporter gene can be produced from the initiation codon in a bacterial cell and a loss-of-function mutation in the mutation hotspot sequence or the DNA sequence of interest destroys the function of the reporter gene, (2) an expression vector comprising a promoter operably linked to a DNA construct that comprises a translation initiation codon, a mutation hotspot sequence downstream of the initiation codon, and a bacterial colony reporter gene downstream of the mutation hotspot sequence, wherein the translation initiation codon, the mutation hotspot sequence, and the reporter gene are arranged in a way so that a protein that comprises the amino acid sequence encoded by the reporter gene and maintains the function of the protein product of the reporter gene can be produced from the initiation codon in a bacterial cell and a loss-of-fiction mutation in the mutation hotspot sequence destroys the function of the reporter gene, and (3) an expression vector comprising a promoter operably linked to a DNA construct that comprises a translation initiation codon, a multiple cloning site downstream of the initiation codon, and a bacterial colony reporter gene downstream of initiation codon, wherein when a DNA sequence of interest or a mutation hotspot sequence is introduced into the DNA construct at the multiple cloning site a protein that comprises the amino acid sequence encoded by the reporter gene and maintains the function of the protein product of the reporter gene can be produced from the initiation codon in a bacterial cell and a loss-of-function mutation in the DNA sequence of interest or the mutation hotspot sequence destroys the function of the reporter gene, wherein the two expression vectors are (1) and (2), expression vectors (1) and (3), or expression vectors (2) and (3), wherein for each of the expression vectors (1), (2), and (3) the mutation hotspot sequence is selected from the group consisting of $CCN_1N_2N_3GG$, $CGN_1N_2N_3CG$, $GCN_1N_2N_3GC$, and $GGN_1N_2N_3CC$, and wherein $N_1$, $N_2$ and $N_3$ can be any nucleotide; and an instruction manual on using two of said vectors for assessing mutability of a DNA sequence of interest.

5. The kit of claim 4, wherein the reporter gene is a killer gene, the product of which can be lethal to a bacterial cell.

6. The kit of claim 4, wherein the reporter gene is a color gene, the product of which can change the color of a bacterial colony.

7. A kit comprising:
one expression vector selected from the group consisting of
(1) an expression vector comprising a promoter operably linked to a DNA construct that comprises a translation initiation codon, a multiple cloning site downstream of the initiation codon, a mutation hotspot sequence downstream of the initiation codon, and a bacterial colony reporter gene downstream of the mutation hotspot sequence, wherein when a DNA sequence of interest is introduced into the DNA construct at the multiple cloning site, a protein that comprises the amino acid sequence encoded by the reporter gene and maintains the function of the protein product of the reporter gene can be produced from the initiation codon in a bacterial cell and a loss-of-function mutation in the mutation hotspot sequence or the DNA sequence of interest destroys the function of the reporter gene, and (2) an expression vector comprising a promoter operably linked to a DNA construct that comprises a translation initiation codon, a mutation hotspot sequence downstream of the initiation codon, and a bacterial colony reporter gene downstream of the mutation hotspot sequence, wherein the translation initiation codon, the mutation hotspot sequence, and the reporter gene are arranged in a way so that a protein that comprises the amino acid sequence encoded by the reporter gene and maintains the function of the protein product of the reporter gene can be produced from the initiation codon in a bacterial cell and a loss-of-function mutation in the mutation hotspot sequence destroys the function of the reporter gene; and an instruction manual on using one of said vectors for assessing mutability of a DNA sequence of interest.

8. The kit of claim 7, wherein the reporter gene is a killer gene, the product of which can be lethal to a bacterial cell.

9. The kit of claim 7, wherein the reporter gene is a color gene, the product of which can change the color of a bacterial colony.

10. A kit comprising:
one expression vector selected from the group consisting of
  (1) an expression vector comprising a promoter operably linked to a DNA construct that comprises a translation initiation codon, a multiple cloning site downstream of the initiation codon, a mutation hotspot sequence downstream of the initiation codon, and a bacterial colony reporter gene downstream of the mutation hotspot sequence, wherein when a DNA sequence of interest is introduced into the DNA construct at the multiple cloning site, a protein that comprises the amino acid sequence encoded by the reporter gene and maintains the function of the protein product of the reporter gene can be produced from the initiation codon in a bacterial cell and a loss-of-function mutation in the mutation hotspot sequence or the DNA sequence of interest destroys the function of the reporter gene, and
  (2) an expression vector comprising a promoter operably linked to a DNA construct that comprises a translation initiation codon, a mutation hotspot sequence downstream of the initiation codon, and a bacterial colony reporter gene downstream of the mutation hotspot sequence, wherein the translation initiation codon, the mutation hotspot sequence, and the reporter gene are arranged in a way so that a protein that comprises the amino acid sequence encoded by the reporter gene and maintains the function of the protein product of the reporter gene can be produced from the initiation codon in a bacterial cell and a loss-of-function mutation in the mutation hotspot sequence destroys the function of the reporter gene, and
wherein for each of the expression vectors (1) and (2) the mutation hotspot sequence is selected from the group consisting of $CCN_1N_2N_3GG$, $CGN_1N_2N_3CG$, $GCN_1N_2N_3GC$, and $GGN_1N_2N_3CC$, and wherein $N_1$, $N_2$, and $N_3$ can be any nucleotide; and
an instruction manual on using one of said vectors for assessing mutability of a DNA sequence of interest.

11. The kit of claim 10, wherein the reporter gene is a killer gene, the product of which can be lethal to a bacterial cell.

12. The kit of claim 10, wherein the reporter gene is a color gene, the product of which can change the color of a bacterial colony.

* * * * *

SEQUENCE LISTING

```
<160> NUMBER OF SEQ ID NOS: 14

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide

<400> SEQUENCE: 1
ccatcgatgg cacctccggc aaagag                                            26

<210> SEQ ID NO 2
<211> LENGTH: 24
<212> TYPE: DNA
<213> ORGANISM: Artificial
<220> FEATURE:
<223> OTHER INFORMATION: Synthetic oligonucleotide

<400> SEQUENCE: 2
ctaggtgcta gtcgacatgt aata                                              24
```

```
<210> SEQ ID NO 3
<211> LENGTH: 13
<212> TYPE: DNA
<213> ORGANISM: Artificial
<220> FEATURE:
<223> OTHER INFORMATION: Synthetic oligonucleotide

<400> SEQUENCE: 3
agtcaagacc aag                                                        13

<210> SEQ ID NO 4
<211> LENGTH: 18
<212> TYPE: DNA
<213> ORGANISM: Artificial
<220> FEATURE:
<223> OTHER INFORMATION: Synthetic oligonucleotide

<400> SEQUENCE: 4
cgacgaagct tacgctgc                                                   18

<210> SEQ ID NO 5
<211> LENGTH: 15
<212> TYPE: DNA
<213> ORGANISM: Artificial
<220> FEATURE:
<223> OTHER INFORMATION: Synthetic oligonucleotide

<400> SEQUENCE: 5
ccataagggc cattg                                                      15

<210> SEQ ID NO 6
<211> LENGTH: 25
<212> TYPE: DNA
<213> ORGANISM: Artificial
<220> FEATURE:
<223> OTHER INFORMATION: Synthetic oligonucleotide

<400> SEQUENCE: 6
gcatcgatgg cacctcaggc aaaga                                           25

<210> SEQ ID NO 7
<211> LENGTH: 25
<212> TYPE: DNA
<213> ORGANISM: Artificial
<220> FEATURE:
<223> OTHER INFORMATION: Synthetic oligonucleotide

<400> SEQUENCE: 7
gcatcgatgg cacctccggc aaaga                                           25

<210> SEQ ID NO 8
<211> LENGTH: 19
<212> TYPE: DNA
<213> ORGANISM: Artificial
<220> FEATURE:
<223> OTHER INFORMATION: Synthetic oligonucleotide

<400> SEQUENCE: 8
atggcaattc cggcaaaga                                                  19

<210> SEQ ID NO 9
<211> LENGTH: 12
<212> TYPE: DNA
<213> ORGANISM: Artificial
<220> FEATURE:
<223> OTHER INFORMATION: Synthetic oligonucleotide
```

-continued

```
<400> SEQUENCE: 9
gcagcgtaag ct                                                            12

<210> SEQ ID NO 10
<211> LENGTH: 28
<212> TYPE: DNA
<213> ORGANISM: Artificial
<220> FEATURE:
<223> OTHER INFORMATION: Synthetic oligonucleotide

<400> SEQUENCE: 10
ccatcgatgg acttgcattg caaacctg                                           28

<210> SEQ ID NO 11
<211> LENGTH: 27
<212> TYPE: DNA
<213> ORGANISM: Artificial
<220> FEATURE:
<223> OTHER INFORMATION: Synthetic oligonucleotide

<400> SEQUENCE: 11
gtcgactcac cctgaggcct tctgttc                                            27

<210> SEQ ID NO 12
<211> LENGTH: 26
<212> TYPE: DNA
<213> ORGANISM: Artificial
<220> FEATURE:
<223> OTHER INFORMATION: Synthetic oligonucleotide

<400> SEQUENCE: 12
tcgatggcac ctcggcaaag agagcc                                             26

<210> SEQ ID NO 13
<211> LENGTH: 27
<212> TYPE: DNA
<213> ORGANISM: Artificial
<220> FEATURE:
<223> OTHER INFORMATION: Synthetic oligonucleotide

<400> SEQUENCE: 13
tcgatggcac ctccggcaaa gagagcc                                            27

<210> SEQ ID NO 14
<211> LENGTH: 23
<212> TYPE: DNA
<213> ORGANISM: Artificial
<220> FEATURE:
<223> OTHER INFORMATION: Synthetic oligonucleotide

<400> SEQUENCE: 14
ggtacgatgg cacctccggc aaa                                                23
```